US007368272B1

(12) United States Patent
Affolter et al.

(10) Patent No.: US 7,368,272 B1
(45) Date of Patent: May 6, 2008

(54) EXPRESSION OF PROTEOLYTIC ENZYMES IN KOJI MOLD IN THE PRESENCE OF CARBON SOURCES

(75) Inventors: Michael Affolter, Pully (CH); Johannes De Reu, Cheseaux (CH); Peter Van Den Broek, Epalinges (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/936,367

(22) PCT Filed: Mar. 2, 2000

(86) PCT No.: PCT/EP00/01796

§ 371 (c)(1), (2), (4) Date: Jan. 23, 2002

(87) PCT Pub. No.: WO00/53725

PCT Pub. Date: Sep. 14, 2000

(30) Foreign Application Priority Data

Mar. 11, 1999 (EP) .................................. 99104923

(51) Int. Cl.
C12N 1/14 (2006.01)
C12N 9/62 (2006.01)
C12P 21/06 (2006.01)

(52) U.S. Cl. .................. 435/212; 435/183; 435/195; 435/223; 435/219; 435/69.1; 435/71.1; 435/254.1; 435/254.3

(58) Field of Classification Search ................ 435/223, 435/183, 195, 212, 219, 69.1, 254.1, 254.3, 435/71.1
See application file for complete search history.

(56) References Cited

U.S. PATENT DOCUMENTS

| 4,308,284 | A | 12/1981 | Noda et al. |
| 5,141,756 | A | 8/1992 | Bajracharya et al. |
| 5,141,757 | A | 8/1992 | Ho Dac et al. |
| 6,020,009 | A | 2/2000 | Wood et al. |

FOREIGN PATENT DOCUMENTS

| EP | 0417481 | | 3/1991 |
| EP | 0429760 | | 6/1991 |
| EP | 0818153 | | 1/1998 |
| EP | 0897003 | | 2/1999 |
| JP | 7115969 | * | 5/1995 |
| WO | WO99/0291 | | 1/1999 |
| WO | WO 9902691 | * | 1/1999 |

OTHER PUBLICATIONS

Dowzer, et al., Molecplar and Cellular Biology, (Nov. 1991) 11 (11) 5701-9.*
Shroff et al., Fungal Genetics and Biology, (Aug. 1997) 22 (1) 23-38.*
Ruijter et al., FEMS Microbiology Letters, (Jun. 15, 1997) 151 (2) 103-14.*
Ruijter et al., MICROBIOLOGY, (Sep. 1997) 143 ( PT 9) 2991-8.*
Van Der Veen, et al., Microbiology (Reading), (1995) vol. 141, No. 9, pp. 2301-2306., abstract.*
Van Den Hombergh et al., GENE. (Dec. 30, 1994) 151 (1-2) 73-9.*
Jarai et al., Current Genetics, (Sep. 1994) 26 (3) 238-44., abstract.*
Dowzer et al., "Analysis of the creA Gene, a Regulator of Carbon Catabolite Repression in *Aspergillus nidulans*," Molecular and Cellular Biology, vol. 11, pp. 5701-5709, Nov. 1991.
Shroff et al., "Null Alleles of creA, the Regulator of Carbon Catabolite Repression in *Aspergillus nidulans*," Fungal Genetics and Biology, vol. 22, pp. 28-38, 1997.
Ruijter et al., "Carbon repression in Aspergilli," FEMS Microbiology Letters, vol. 151, pp. 103-114, 1997.
Ruijter et al., "Isolation of *Aspergillus niger* creA mutants and effects of the mutations on expression of arabinases and L-arabinose catabolic enzymes," Microbiology, vol. 143, pp. 2991-2998, 1997.
Van Der Veen et al., "An extreme creA mutation in *Asperigillus nidulans* has severe effects on D-glucose utilization," retrieved from STN, XP002125189, abstract, Microbiology (Reading), vol. 141, pp. 2301-2306, 1995.
Van Den Hombergh et al., "Cloning characterization and expression of pepF, a gene encoding a serine carboxypeptidase from *Aspergillus niger*," Gene., vol. 151, pp. 73-79, 1994.
Jarai et al., "Nitrogen, carbon, and pH regulation of extracellular acidic proteases of *Aspergillus niger*," retrieved from STN, XP002125190, abstract, Current Genetics, vol. 26, pp. 238-244, 1994.
Database WPI, XP002125191, Asahi Kasei Koyo KK, May 9, 1995, abstract.
Doumas et al., "Characterization of the Prolyl Dipeptidyl Peptidase Gene (dpplV) from the Koji Mold *Aspergillus cryzae*," Applied and Environmental Microbiology, vol. 64, pp. 4809-4815, 1998.
Katz, et al., "Isolation and characterization of an *Aspergillus nidulans* gene encoding an alkaline protease," Gene., vol. 150, pp. 287-282, 1994.
Arst, et al., "Nitrogen Metabolite Repression in *Aspergillus nidulans*," Molec. gen. Genet., vol. 126, pp. 111-141, 1973.
Drysdale et al., "The *Aspergillus niger* carbon catabolite repressor encoding gene, creA," Gene., vol. 130, pp. 241-245, 1993.
Yanisch-Perron et al., "Improved M13 phage cloning vectors and host strains: nucleotide sequences of the M13mp18 and pUC19 vectors," Gene., vol. 33, pp. 109-119, 1985.
Samson, ed. Bennett and Klich, "Current Taxonomic Schemes of the Genus Aspergillus and Its Teleomorphs," Biology and Industrial Applications, pp. 355-390, 1992.
Maniatis, A Laboratory Manual, Chapter 4, Single-stranded, Filamentous Bateriophage Vectors, Molecular Cloning, 1989, vol. 1.

* cited by examiner

*Primary Examiner*—Chih-Min Kam
(74) *Attorney, Agent, or Firm*—Bell, Boyd & Lloyd LLP

(57) ABSTRACT

The present invention refers to a koji mold capable of expressing proteolytic enzymes in the presence of a carbon source in at least the same amount as in the absence thereof. In particular, the present invention pertains to a mutation in the creA gene as a tool to increase the amount of a wide spectrum of proteolytic enzymes in the presence of a carbon source.

6 Claims, 1 Drawing Sheet

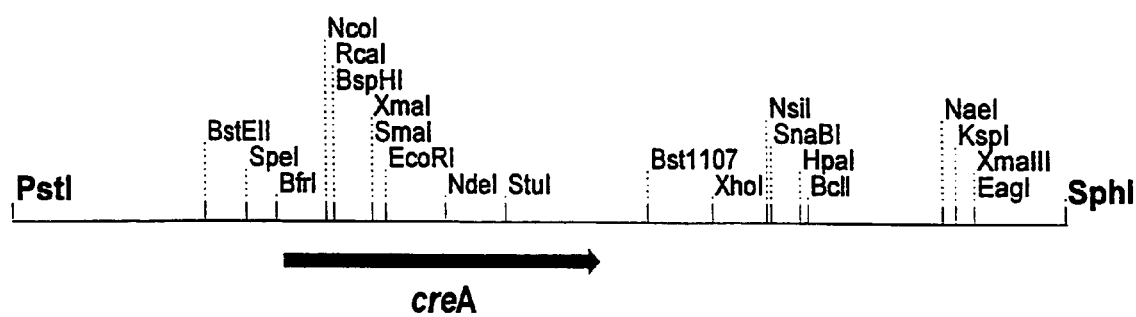
Figure 1. Restriction map of the *Aspergillus oryzae* creA gene.

SEQUENCE LISTING

<160> NUMBER OF SEQ ID NOS: 5

<210> SEQ ID NO 1
<211> LENGTH: 4238
<212> TYPE: DNA
<213> ORGANISM: Aspergillus oryzae -continued

```
<400> SEQUENCE: 1
ctgcagttcc agtttctacc ccgtaaatcc ctatcaactt agtccgcccc acattctttt      60
ttttttttcc ttttttttc gctcccggtc agagtgatag tgggatttat tacacaccgt      120
gcgtggtcga agaacgacac ggaagaagcc ccggaagacg ccttctctag caacaaatg      180 attgtactct tatgatactc aatacggtag aaaatagaga attgagatac gaaagctgac      240
tcatcagaac agaataaggg gaattttga ttagcaaata acaataataa ttatacaaaa      300
aaacaaataa aaaatttag gggactcccc acccgctgta atcctgggtg tatctcaaag      360
caaagcaggc gatctggggg gagcacgttc tttttttttc ttttctcttt tttctattt      420 tttttttt tttattttag gtctatgcct ttttttttct tttccttttt tttttttt      480 tttgccccc gataattctc cccacacata ggacatactt tttttttttt tccttccact      540
cccttcaagg tctccgattc cgataacccc ctctaccagt tcgccctgcc tttttctctc      600 ccctccccg aagctccatt tctctcttct tcccctccat tcctcattct tcctcttccg      660
tatttccttt atatgctcct atccccagac catttctcca gatttctctc tctttcccct      720
ctctcccttt cgacaaattg ttgcttgact acatccatct cgggttacct acttacagta      780
ccaattccgg atatactcta tcccacccat caccacattc cataacagcg cccttttcatt      840 gggaaagtca ctcttccttg aaattggtta catcgcggac atcgtacct tctttaatcg      900 caaggcttgt gatactcttg cggtgctcgt tcatcaacta gtactttgcc aagagcaagt      960
ctccgtcttg tcgggtggtg atcgactctc cccgatttac ctaccctgt tgcgacgaat     1020 cctgattcgc ctcggctcgt cagcccttcc gagcttccct taagtacagg cttcgtcccc     1080
tctttagctg cactcctcgg tgctaggtta ggacgagtca catgccacca ccggcttctt     1140
cagtggattt caccaatctg ctgaaccctc agaataacga gactggttct gcaccttcca     1200
cgccagtgga tagctccaag gctccctcta ccccgtccag tactcagtcc aactctacca     1260
tggcctcgtc tgttagctta ctaccgcccc tcatgaaggg tgctcgtccc gcaacggaag     1320
aagcgcgcca ggatcttccc cgtccataca agtgtcccct gtgtgatcgc gccttccatc     1380
gtttggagca ccagaccaga catattcgca cacatacggg tgaaaagcca cacgcttgcc     1440
agttcccggg ctgcacaaaa cgctttagtc gctctgacga gctgacacgc cactcaagaa     1500
ttcacaacaa ccccaactcc aggcggagta acaaggcaca tctggccgct gccgctgccg     1560
ctgccgctgc cggacaagag aatgcaatgg taaatgtgac caacgcgggc tcgttgatgc     1620
ccccgcccac aaagcctatg acccgctctg cgcctgtctc tcaggttgga tctccggatg     1680
tctcccctcc gcactccttc tcgaactatg ccggtcacat gcgttccaat ctgggaccat     1740
atgctcgcaa caccgagcgg gcgtcctcgg gaatggatat caatctactt gccaccgctg     1800
catctcaggt tgagcgtgat gaacaacatt ttgggttcca cgctggtcca cgtaatcacc     1860
atttgttcgc ctcgcgtcac cacaccggtc gtggcctgcc ttcccttca gcgtacgcca     1920 tctcgcacag catgagccgt tctcactttc acgaggacga ggatggttac actcatcgcg     1980
tcaagcgctc aaggcctaac tcaccaaact cgaccgctcc gtcctcaccg actttctctc     2040
acgactctct ttccccaacg ccagaccaca ctccgttggc aacccctgct cattcgccac     2100
gcttgaggtc attgggatct agcgaactcc accttccttc gattcgccat ctgtccctcc     2160
atcacacccc tgcccttgct ccaatggagc cccagccgga aggccccaac tattacagtc     2220
ccagccagtc tcatggtccc acaatcagcg atatcatgtc cagacccgac ggaacacagc     2280
gtaaactgcc cgttccacag gttcccaagg tcgcggtgca agatatgctg aaccccagcg     2340
```

-continued

```
ctgggttttc gtcggtttcc tcatcgacga ataactctgt cgcaggaaat gatttggcag    2400
aacgtttcta gcctggtgcg gctgcgaaac cctttcaatg tataaagttt tgggctcaaa    2460
aaaaattctt gactgtcata cgcgctacga acgaataga ctttgtgcat ttacagtgcg     2520
tggttcatgg gcatccttgg tgtcggctgg cttctttgc ttactttgtt cgagtatact     2580
tttgcgaggc gtccatagtg atagacgggt gggatattct tgtggctttt tccgtgcttg    2640
ttcgattctc ccctttcgct ctccttgaaa atacctttc ttatcctata accatttgtt    2700
tcattatccc aatgggaatt ggctctacag ctcttattca ttttgtctac tcctctcctg    2760
aggcccagtc ccctgataat tccgggctct accatataca tttcatttcg actatgtcag    2820
tttccgcttc gatttagacc tcgagcagga cgagagggtt ccgaaagaaa atacaaacaa    2880
aaattatagt aatctgcgtt tactttggca taatacagta gtcattagtt gaggtaggca    2940
taatctggat gtctaaccat cacttgccct aacctcctac catctgctgc tagtatttgt    3000
cttacccgaa acccaattca acgagataga tggattgacg aataacaatt tgttgtccag    3060
cgacatgcat gatacatgcg tacgtacata cactaatagt agtcacagac cagttcatca    3120
catcctggtc tcgggtattc agatacggaa atgcgtaaga ttggaagggt ctaagaaaaa    3180
gcaaagaaaa aggaaaagtt aacactggcg ggcgctctct ttccatctct gatcaatgtt    3240
attgttcgtc actcagctgt ggacgtggct ccagtcaagt tgtgaattat datagggtat    3300
tgttgacttg acaagttgat cttgatgaa tcaaatcttc tccccgccag attctgacgc     3360
ttgaggctct cggatcgaat gaacaacttt tcgcaccaca tcaaccggtt gccgcgtgat    3420
gctggagaca aaccgaccca aacgtcacgg tcacacggag gatacgttg ctagagccag     3480
ctgataccc aagagacaag aaggtaaagg tcgcaaaaat cttttcaata agatggcatc    3540
ttcccccac caacccttaa ccattctcct ttcaagctgt gttgccccgc tttggtgcat    3600
gggcttgggt agtgcggtcg caaaactact aatttaatga ccgactgctg ctgcttttc    3660
actcgccgct cacggactaa gcatgtggga acaggatcgc cccgtcacta tttcagatcg   3720
tgtcgtatca aggtgttcgc ccggtgctgc tggcacgaac gccggccatc caagatcatt   3780
gttctcattc aaaccgggcg gcttacgtct agccgcggac gtaagcacga agagtgtgtg  3840
tagtggtggg agtgaagccg ttgccgaaac catgccgtcc tccacggccg tcccgtcgtt  3900
atcaagcgac gctgcctccg cttcatcctc atcagcgggt gtatctctgg agacaagatg  3960
ggcggaaggt ctcaccggcc aggagatatt agaagacgat ggaacgggcg cgctcgtcgt  4020
cccgccgtcc cgccctgctc ggcaatatca tcaccatacc tatatctgtc tgttctatat  4080
cttagattgt caccacacct tcgacgatgt cgagcaatgg aagactcacg ttctgagcca  4140
cttccgaacc cacgaaccac cgcgaacagc ccgatgccct ctatgtccgg gtgagcggtt  4200
cagcgacacc cccgaacaga aaggatggga tcgcatgc                          4238
```

<210> SEQ ID NO 2
<211> LENGTH: 431
<212> TYPE: PRT
<213> ORGANISM: Aspergillus oryzae

<400> SEQUENCE: 2

Met Pro Pro Pro Ala Ser Ser Val Asp Phe Thr Asn Leu Leu Asn Pro
1               5                   10                  15

Gln Asn Asn Glu Thr Gly Ser Ala Pro Ser Thr Pro Val Asp Ser Ser
            20                  25                  30

```
Lys Ala Pro Ser Thr Pro Ser Ser Thr Gln Ser Asn Ser Thr Met Ala
        35                  40                  45

Ser Ser Val Ser Leu Leu Pro Pro Leu Met Lys Gly Ala Arg Pro Ala
 50                  55                  60

Thr Glu Glu Ala Arg Gln Asp Leu Pro Arg Pro Tyr Lys Cys Pro Leu
 65                  70                  75                  80

Cys Asp Arg Ala Phe His Arg Leu Glu His Gln Thr Arg His Ile Arg
                 85                  90                  95

Thr His Thr Gly Glu Lys Pro His Ala Cys Gln Phe Pro Gly Cys Thr
            100                 105                 110

Lys Arg Phe Ser Arg Ser Asp Glu Leu Thr Arg His Ser Arg Ile His
            115                 120                 125

Asn Asn Pro Asn Ser Arg Arg Ser Asn Lys Ala His Leu Ala Ala Ala
130                 135                 140

Ala Ala Ala Ala Ala Gly Gln Gly Gln Glu Asn Ala Met Val Asn
145                 150                 155                 160

Val Thr Asn Ala Gly Ser Leu Met Pro Pro Thr Lys Pro Met Thr
                165                 170                 175

Arg Ser Ala Pro Val Ser Gln Val Gly Ser Pro Asp Val Ser Pro Pro
            180                 185                 190

His Ser Phe Ser Asn Tyr Ala Gly His Met Arg Ser Asn Leu Gly Pro
            195                 200                 205

Tyr Ala Arg Asn Thr Glu Arg Ala Ser Ser Gly Met Asp Ile Asn Leu
            210                 215                 220

Leu Ala Thr Ala Ala Ser Gln Val Glu Arg Asp Glu Gln His Phe Gly
225                 230                 235                 240

Phe His Ala Gly Pro Arg Asn His His Leu Phe Ala Ser Arg His His
                245                 250                 255

Thr Gly Arg Gly Leu Pro Ser Leu Ser Ala Tyr Ala Ile Ser His Ser
            260                 265                 270

Met Ser Arg Ser His Phe His Glu Asp Glu Asp Gly Tyr Thr His Arg
            275                 280                 285

Val Lys Arg Ser Arg Pro Asn Ser Pro Asn Ser Thr Ala Pro Ser Ser
            290                 295                 300

Pro Thr Phe Ser His Asp Ser Leu Ser Pro Thr Pro Asp His Thr Pro
305                 310                 315                 320

Leu Ala Thr Pro Ala His Ser Pro Arg Leu Arg Ser Leu Gly Ser Ser
                325                 330                 335

Glu Leu His Leu Pro Ser Ile Arg His Leu Ser Leu His His Thr Pro
            340                 345                 350

Ala Leu Ala Pro Met Glu Pro Gln Pro Glu Gly Pro Asn Tyr Tyr Ser
            355                 360                 365

Pro Ser Gln Ser His Gly Pro Thr Ile Ser Asp Ile Met Ser Arg Pro
370                 375                 380

Asp Gly Thr Gln Arg Lys Leu Pro Val Pro Gln Val Pro Lys Val Ala
385                 390                 395                 400

Val Gln Asp Met Leu Asn Pro Ser Ala Gly Phe Ser Ser Val Ser Ser
                405                 410                 415

Ser Thr Asn Asn Ser Val Ala Gly Asn Asp Leu Ala Glu Arg Phe
                420                 425                 430

<210> SEQ ID NO 3
<211> LENGTH: 29
<212> TYPE: DNA
```

```
<213> ORGANISM: Artificial
<220> FEATURE:
<223> OTHER INFORMATION: Oligonucleotide

<400> SEQUENCE: 3
cttccccgtc catagtagtg tcccctgtg                                29

<210> SEQ ID NO 4
<211> LENGTH: 29
<212> TYPE: DNA
<213> ORGANISM: Artificial
<220> FEATURE:
<223> OTHER INFORMATION: Oligonucleotide

<400> SEQUENCE: 4
cacaggggac actactatgg acggggaag                                29

<210> SEQ ID NO 5
<211> LENGTH: 6
<212> TYPE: PRT
<213> ORGANISM: Artificial
<220> FEATURE:
<223> OTHER INFORMATION: consensus of creA DNA-binding site

<400> SEQUENCE: 5

Ser Tyr Gly Arg Gly Gly
1               5
```

EXPRESSION OF PROTEOLYTIC ENZYMES IN KOJI MOLD IN THE PRESENCE OF CARBON SOURCES

This application is a 371 of PCT/EP00/01796, filed Mar. 2, 2000, which claims the foreign priority of EPO 99104923.0, filed Mar. 11, 1999.

The present invention refers to koji molds capable of expressing proteolytic enzymes in the presence of a carbon source in at least the same amount as in the absence thereof. In particular, the present invention pertains to a modification of the expression of the creA gene product as a tool to increase the amount of a wide spectrum of proteolytic enzymes in the presence of a carbon source.

STATE OF THE ART

Hydrolyzed proteins, which are widely used in the food industry, may be prepared by hydrolytic degradation of protein material with acid, alkali or enzymes. As regards a treatment of the material with acid or alkaline this procedure has been shown to also destroy essential amino acids generated during hydrolysis thus reducing the nutritional value of the final product. On the other hand hydrolysis by addition of enzymes rarely goes to completion so that the hydrolyzed protein material still contains substantial amounts of peptides. Depending on the nature of the protein and the enzymatic components utilized for proteolysis, the peptides formed may, however, lead to extremely bitter tastes and are thus organoleptically undesirable.

In some methods instead of chemical or isolated biological material microorganisms as such are employed for this purpose. In these cases the proteinaceous material available is hydrolyzed by the action of a large variety of enzymes, such as amylases, proteinases, peptidases etc., that are secreted by the microorganism.

One class of such microorganisms are koji molds that are traditionally used for making koji cultures (see e.g. U.S. Pat. No. 4,308,284). These molds comprise e.g. microorganisms of the genus *Aspergillus, Rhizopus* and/or *Mucor*, in particular *Aspergillus soyae, Aspergillus oryzae, Aspergillus phoenicis, Aspergillus niger, Aspergillus awamori, Rhizopus oryzae, Rhizopus oligosporus, Rhizopus japonicus, Rhizopus formosaensis, Mucor circinelloides, Mucor japanicus, Penicillium glaucum* and *Penicillium fuscum*.

According to the rules of the International Code of Botanical Nomenclature (ICBN), *Aspergillus* is an anamorphic genus. This means that true *Aspergilli* only reproduce asexually through conidiophores. However, the typical *Aspergillus* conidiophore morphology may also be found in fungi that may reproduce sexually via ascospores. Some *Aspergillus* taxonomists caused confusion, because they did not adhere to ICBN terminology. Instead, they attempted to make various revisions of taxonomical schemes to include *Aspergillus nidulans* in this genus, despite the fact that its taxonomically correct name is *Emericella nidulans* (Samson, In: *Aspergillus*. Biology and Industrial Applications, pp 355-390, ed. by Bennett and Klich, Boston). In effect, the microorganism termed *Aspergillus nidulans* may be considered not to belong to the genus *Aspergillus* itself.

In EP 0 417 481 a process for the production of a fermented soya sauce is described, wherein a koji is prepared by mixing a koji culture with a mixture of cooked soya and roasted wheat. The koji thus obtained is then hydrolyzed in an aqueous suspension for 3 to 8 hours at 45° C. to 60° C. with the enzymes produced during fermentation of the koji culture, a moromi is further prepared by adding sodium chloride to the hydrolyzed koji suspension, the moromi is left to ferment and is then pressed with the liquor obtained being pasteurized and clarified.

EP 0 429 760 describes a process for the production of a flavoring agent in which an aqueous suspension of a protein-rich material is prepared, the proteins are solubilized by hydrolysis of the suspension with a protease at pH 6.0 to 11.0, the suspension is heat-treated at a pH of 4.6 to 6 and is subsequently ripened with enzymes of a koji culture.

Likewise, European patent application 96 201 923.8 describes a process for the production of a meat flavor, in which a mixture containing a vegetal proteinaceous source and a vegetal carbohydrates containing source is prepared, said mixture having initially at least 45% dry matter, the mixture is inoculated with a koji culture and by one or more other species of microorganisms involved in the traditional fermentation of meat, and the mixture is incubated until meat flavors are formed.

Yet, all the processes involving the use of different microorganisms also show the disadvantage that the protein material is not hydrolysed completely while a longer incubation of the material with the microorganisms to achieve a substantial hydrolysis may lead to the formation of unwanted metabolic side products.

Thus there exists a need in the art for optimizing said hydrolysis processes. Yet, said optimization and further development of koji processes have been seriously hampered by the lack of knowledge on the nature of the hydrolytic enzymes involved, their regulation and the influence of process parameters on their expression and activity, e.g. temperature, pH, water activity and salt concentration.

From Katz et al., Gene 150 (1994), 287-292 it is known that in the fungi *Emericella nidulans* the expression and secretion of proteolytic enzymes, that are inherently used by the microorganism to provide the nitrogen-, sulfur- and carbon sources required for its proliferation, is subject to at least three general control circuits including carbon catabolite repression, nitrogen- and sulfur-metabolite repression.

These three regulatory circuits ensure that the available nitrogen-, carbon- and sulfur-sources in a substrate are utilized sequentially according to their nitrogen-, energy- and sulfur-yield. Nitrogen metabolite repression has been found to be inter alia exerted by the areA gene product in *Emericella nidulans* (Arst et al., Mol. Gen. Genet. 26 (1973), 111-141,), whereas in other fungi it is assumed that possibly other genes are deemed to be responsible for said function. In fact, most fungi that have been studied seem to have an areA homologue performing said function.

In wheat bran fermentations performed with *Aspergillus oryzae*, proteolytic activity could only be detected when the glucose concentration dropped below a certain threshold. These observations suggest that any expression of proteolytic enzymes in *A. oryzae* is not induced by the presence of proteins but seems to be merely carbon-derepressed. During a fermentation process utilising soy kojis a significant amount of glucose has been found to be liberated as result of amylase activity which eventually results in a carbon catabolite repression of protease-encoding genes.

Hence, there is a need for an improved method for hydrolyzing proteins leading to high degree of protein hydrolysis and to hydrolysates with excellent organoleptic properties.

SUMMARY OF THE INVENTION

This object has been solved by providing a koji mold belonging to the genus *Aspergillus, Rhizopus, Mucor* or *Penicillium*, the proteolytic activity of which is not carbon repressed.

According to the invention, in said microorganisms the expression of the creA gene has been modified such that the gene product thereof gives rise to a polypeptide exhibiting a decreased or no binding affinity at all to DNA sequences responsible for blocking the transcription of proteases.

In another preferred embodiment the synthesis of the creA gene is modified in such a way that the corresponding gene product is substantially not transcribed or not transcribed at all or not translated to a functional product. This may e.g. be achieved by means of introducing a construct into the genome of the microorganism that gives rise to a creA anti-sense mRNA thus preventing translation of the creA gene into a functional polypeptide. On the other hand also mutations may be introduced into the creA gene so that no transcription takes place. Eventually, the creA gene may also be entirely deleted so that no repression takes place in the presence of a carbon source.

The mutations leading to the microorganism having the desired traits may be obtained via classical techniques, such as mutation and selection or by using genetic engineering techniques, with which a selective mutation in the creA gene may be achieved.

In addition, a creA mutation may also be combined with the property of an increased production of the areA gene, a positive stimulator for the production of proteases.

DETAILED DESCRIPTION OF THE INVENTION

In the Figures:

FIG. 1 is a restriction map of a % Gem12 clone. The coding region was localised on a 4.3 kB PstI-SpHI fragment that was subcloned in pUC19.

Theoretically, generating mutations in the creA gene, that diminish or even interrupt binding of the gene product thereof to the corresponding DNA sequences should lead to an earlier onset of protease production in wheat bran kojis, resulting in a higher protease yield and thus to an increased secretion of proteases. Also, in soy kojis creA mutations would theoretically alleviate carbon catabolite repression of protease production and should result in higher protease production.

Yet, in Gene 130 (1993), 241-245 M. Drysdale et al. reported that in *A. nidulans* a deletion of the creA gene together with flanking sequences leads to a lethal phenotype. It was therefore assumed that in addition to its role as a repressor protein creA has still other viable regulatory roles without which the microorganism is not capable to proliferate and grow.

In contrast to this general belief the present inventors have surprisingly found that it is in fact possible to create viable creA mutants, that are capable to express a wide variety of different proteolytic enzymes even in the presence of a carbon source.

In order to achieve this objective the following procedure has been adopted.

It has been assumed that creA mutants may be isolated as areA suppressor mutations. The areA gene is one of several genes involved in the activation of the transcription of a wide variety of proteolytic polypeptides. The areA gene is controlled by the presence or absence of intracellular glutamine, which in effect represents a nitrogen dependent control.

*A. oryzae* NF2 (CNCM 1882), an areA null-mutant described in detail in EP 97111378.2, which document is incorporated herein by way of reference, has been shown to be unable to grow on minimal medium (see below) containing 0.2% soy protein and 50 mM glucose. The same mutant was also incapable to grow in wheat gluten koji.

In an areA null-mutant, the areA gene product no longer stimulates the transcription of protease encoding genes, resulting in the microorganisms to exhibit a decreased protease secretion.

In addition, in the presence of a carbon source, such as glucose, fructose or saccharose, the creA gene product represses transcription of protease encoding genes eventually resulting in an incapability of the areA null mutant to use protein as a nitrogen source. Consequently, area null mutants with an operative creA gene should be unable to proliferate and grow in such an environment.

In order to isolate creA mutants, areA null mutants of *A. oryzae* may be subjected to mutagenic agents in the above mentioned medium (0.2% soy protein, 50 mM glucose), such as e.g. UV irradiation, treatment with EMS (Ethyl methane sulfonate), methyl methane sulfonate or DMSO, nitrosoguanidine, etc.

Theoretically, in at least some colonies that are capable to grow on the medium the creA gene should have been mutated such that the gene product thereof may not exert its normal action thus allowing for the growth in such a medium (see above).

The colonies may then be analysed for the presence of an increased proteolytic activity, which may be achieved e.g. by means of determining the activity of enzymes that are under control of creA, such as alcohol dehydrogenase, amylase, acetamidase etc.

For example, colonies growing in the above referenced medium may be investigated for hypersensitivity towards Fluor-acetate. In wild type strains an active creA protein prevents the induction of acetate utilisation enzymes in the presence of glucose. Under this condition Fluor-acetate is not metabolised. Yet, in creA mutants, in which the creA gene product does not take over its inherent function, these acetate utilisation enzymes are transcribed in an essentially constitutive manner. As a result, Fluor-acetate will be converted to compounds that are toxic for the microorganisms. The visual result resides in that strains, having a mutation in the creA gene which renders the gene product essentially ineffective, will not grow in a medium containing Fluor-acetate and a carbon source.

CreA mutants may also be identified according to their hypersensitivity towards allyl-alcohol in the presence of a carbon source. In wild type strains the active creA protein normally prevents the induction of alcohol dehydrogenase, that oxidises the above substrate to ketone acreoline, a compound toxic for the microorganism. Under repressive conditions, i.e. in the presence of a carbon source, the allyl-alcohol will normally not be oxidised to the toxic compound due to creA exerting its inherent function to repress the transcription of alcohol dehydrogenase. However, in mutants in which the creA gene is not functional any more, alcohol dehydrogenase is essentially expressed constitutively, intoxicating the mould with acreoline even in the presence of the carbon source.

In addition to the above random mutagenesis of an areA null mutant by mutagenic agents and selection for the desired trait the creA gene may also be modified in a suitable way by means of genetic engineering.

To this end, a construct may be incorporated in the moulds' genome, comprising a DNA sequence being transcribed into an anti-sense RNA to creA. This may be achieved by techniques well known in the art such as is e.g. described in Maniatis, A Laboratory manual, Cold Spring Harbor, 1992. This option provides for the advantage that the action of the anti-sense RNA itself may be controlled in a suitable way by rendering the transcription dependent on the presence or absence of particular molecules known to induce transcription in a given system. Vectors to clone a given DNA fragment as well as promoters and their way of induction are well known in the art and may e.g. be found in Maniatis, supra.

Further, the creA gene may well be modified in such a way that the gene product thereof is substantially or even entirely ineffective. This may be effected by introducing mutations into the DNA sequence so that the corresponding polypeptide looses its capability of exerting its regulatory action by e.g. binding to the corresponding regulatory DNA sequences. Moreover, the creA gene may partly or even entirely be deleted so that no repression takes place at all in the presence of a carbon source.

It has now been found that in spite of the difference in relation the creA gene of *A. oryzae* may be is isolated using a DNA sequence comprising the coding region of the corresponding gene of *Aspergillus nidulans* as a probe, however, applying low stringent conditions during hybridisation.

Due to the low stringency conditions applied a plurality of different colonies were initially isolated which could subsequently be excluded by increasing the conditions of stringency.

After having isolated DNA of strongly hybridising colonies the complete *A. oryzae* creA gene could be assigned to a 4.3 KB PstI-SphI fragment, which could be cloned into a suitable vector, such as a plasmid or a viral vector and sequenced. The sequence obtained thereby is shown under SEQ ID NO I, below.

In analysing the DNA sequence a potential open reading frame could be found yielding a polypeptide having the amino acid sequence identified as SEQ ID NO II, below The DNA sequence thus identified may then be used to introduce specific mutations into the creA gene. This may be effected by e.g. cloning the fragment in a suitable vector, such as the high copy number vector pUC or M13, deleting part of the coding sequences or introducing a stop codon in the reading frame and introducing the modified creA gene into an areA mutant, like *A. oryzae* NF2 (CNCM 1882). CreA-areA double mutants can then be selected on minimal medium (below) containing protein (i.e. 0.2% soy) and 50 mM glucose by their ability to grow, whereas an areA mutant will not grow.

In determining for an effective transfer of a suitably modified construct in a wild type background a marker such as e.g. a resistance gene may be utilised, that may be deleted from the moulds' genome after having isolated a creA mutant having the desired traits. Techniques for cloning, introducing mutations and/or deletions into a given gene and for introducing DNA sequences into a microorganism are known in the art and may be e.g. found in Maniatis et al., supra.

The following examples further illustrate the invention.

Strains & Plasmids

*A. nidulans* G332 (pabaA1, yA2, xprD1), used to amplify the creA gene, —was obtained from the Glasgow Genetic Stock Centre via Dr. A. J. Clutterbuck. *A. oryzae* TK3 (aflR1, omtA1), were obtained from the strain collection of the Nestlé Research Center Lausanne. *A. oryzae* NF1 (pyrG1) is a uridine auxotroph derivative of *A. oryzae* TK3 in which the pyrG gene, encoding orotidine 5'-phosphate decarboxylase, was inactivated by targeted disruption. *A. oryzae* NF2 (CNCM 1882) is an areA disruption mutant, derived from *A. oryzae* NF1 as described in EP 97111378.2.

The vector LambdaGem-12 was obtained from Promega, pUC19 (Yanisch-Perron C., Vieira, J. and Messing, J. Improved M13 phage cloning vectors and host strains: nucleotide sequences of M13 mp18 and pUC19; Gene 33 (1985), 103-119) was obtained from New England Biolabs Inc. USA.

Media

Minimal medium (MM) contains per liter 1.5 $KH_2PO_4$ (Merck, Darmstadt, FRG), 0.5 g $MgSO_4.7H_2O$ (Merck, Darmstadt, FRG), 0.5 g KCl (Merck). For selection of mutants 50 mM Glucose ((Merck, Darmstadt, FRG), 0.2% Soy Protein (Protein Technologies International) and 2% agar noble were added to MM. Protease plate assays were performed either on MM with 0.08% sodium desoxycholate (Fluka, Buchs, Switzerland) and 0.2% soy protein as sole carbon and nitrogen source or on MM with 1% skimmed milk (Difco) and 2% agar noble (Difco)

EXAMPLE 1

Isolation of creA Mutants

To isolate creA mutants relevant to the production of proteolytic activity, areA null mutants have been created as described in EP 97111378.2. Further, 108 conidiospores of *A. oryzae* NF2 (CNCM 1882) were UV irradiated (500 mJ/cm2 254 nm, 50% survival) and plated on minimal medium containing 0.2% soy protein, 50 mM glucose and 2% agar noble (Difco). Four sporulating colonies, termed NF14 to NF17 were selected, that were found to be sensitive to 15 mM allyl alcohol in the presence of 50 mM glucose, suggesting that these four mutants were creA mutations. Furthermore, NF14 to NF17 were shown to secrete proteases in the presence of glucose.

The *Aspergillus oryzae* mutant was deposited on Mar. 9, 1999, according to the Budapest Treaty with an International Depository Authority: the Institute Pasteur at 25 Rue du Docteur Roux F-75724 Paris, France. The deposit is identified as NF14 (are A1, cre A1) and is assigned Deposit No. CNCM I-2165. All restrictions on the availability to the public of the material so deposited will be irrevocably removed upon the grant of a patent.

EXAMPLE 2

Isolation of the creA Gene

A genomic library of *Aspergillus oryzae* TK3 (supra) in GEM 12 was screened under low stringency conditions (55° C., 5×SSC, 1% SDS) with a 1.3 KB PCR product encompassing the coding region of the *A. nidulans* creA gene.

A total of 100 positive clones were propagated and again hybridised with the probe under conditions of slightly increased stringency by increasing the temperature to about 60° C. In the following three of the most strongly hybridising clones were isolated.

The *A. oryzae* creA gene was subcloned from a Gem12 clone as a 7.3 KB BamHI fragment. By Southern analysis, the coding region was localised on a 4.3 KB PstI-SphI fragment that was subcloned in pUC19 generating pNFF212 and completely sequenced. The nucleotide sequence (SEQ ID NO:1) and deduced amino acid sequence (SEQ ID NO:2) of the *A. oryzae* creA gene is given below. Sequence motifs in the putative promoter region that fit the SYGRGG (SEQ ID NO 5) consensus of CREA DNA-binding sites (Kulmburg et al., 1993) are singly underlined and marked in bold. The region encompassing the DNA-binding $C_2H_2$ Zn finger region in the CREA protein (Dowzer et al., 1989) is doubly underlined and in bold.

```
-1120 CTGCAGTTCCAGTTTCTACCCCGTAAATCCCTATCAACTTAGTCCGCCCCACATTCTTTT -1061
-1060 TTTTTTTTCCTTTTTTTTTCGCTCCCGGTCAGAGTGATAGTGGGATTTATTACACACCGT -1001
-1000 GCGTGGTCGAAGAACGACACGGAAGAAGCCCCGGAAGACGCCTTCTCTAGGCAACAAATG  -941
 -940 ATTGTACTCTTATGATACTCAATACGGTAGAAAATAGAGAATTGAGATACGAAAGCTGAC  -881
 -880 TCATCAGAACAGAATAAGGGGAATTTTTGATTAGCAAATAACAATAATAATTATACAAAA  -821
 -820 AAACAAATAAAAAAATTTAGGGGACTCCCCACCCGCTGTAATCCTGGGTGTATCTCAAAG  -761
 -760 CAAAGCAGGCGATCTGGGGGGAGCACGTTCTTTTTTTTTCTTTTCTCTTTTTTCTATTTT  -701
 -700 TTTTTTTTTTTTTATTTTAGGTCTATGCCTTTTTTTTTCTTTTCCTTTTTTTTTTTTTTT  -641
 -640 TTTGCCCCCCGATAATTCTCCCCACACATAGGACATACTTTTTTTTTTTTCCTTCCACT   -581
 -580 CCCTTCAAGGTCTCCGATTCCGATAACCCCCTCTACCAGTTCGCCCTGCCTTTTTCTCTC  -521
 -520 CCCTCCCCCGAAGCTCCATTTCTCTCTTCTTCCCCTCCATTCCTCATTCTTCCTCTTCCG  -461
 -460 TATTTCCTTTATATGCTCCTATCCCCAGACCATTTCTCCAGATTTCTCTCTCTTTCCCCT  -401
 -400 CTCTCCCTTTCGACAAATTGTTGCTTGACTACATCCATCTCGGGTTACCTACTTACAGTA  -341
 -340 CCAATTCCGGATATACTCTATCCCACCCATCACCACATTCCATAACAGCGCCCTTTCATT  -281
 -280 GGGAAAGTCACTCTTCCTTGAAATTGGTTACATCGCGGACCATCGTACCTTCTTTAATCG  -221
 -220 CAAGGCTTGTGATACTCTTGCGGTGCTCGTTCATCAACTAGTACTTTGCCAAGAGCAAGT  -161
 -160 CTCCGTCTTGTCGGGTGGTGATCGACTCTCCCCGATTTACCTACCCCTGTTGCGACGAAT  -101
 -100 CCTGATTCGCCTCGGCTCGTCAGCCCTTCCGAGCTTCCCTTAAGTACAGGCTTCGTCCCC   -41
  -40 TCTTTAGCTGCACTCCTCGGTGCTAGGTTAGGACGAGTCACATGCCACCACCGGCTTCTT    19
                                                MetProProProAlaSerS
   20 CAGTGGATTTCACCAATCTGCTGAACCCTCAGAATAACGAGACTGGTTCTGCACCTTCCA    79
      erValAspPheThrAsnLeuLeuAsnProGlnAsnAsnGluThrGlySerAlaProSerT
   80 CGCCAGTGGATAGCTCCAAGGCTCCCTCTACCCCGTCCAGTACTCAGTCCAACTCTACCA   139
      hrProValAspSerSerLysAlaProSerThrProSerSerThrGlnSerAsnSerThrM
  140 TGGCCTCGTCTGTTAGCTTACTACCGCCCCTCATGAAGGGTGCTCGTCCCGCAACGGAAG   199
      etAlaSerSerValSerLeuLeuProProLeuMetLysGlyAlaArgProAlaThrGluG
  200 AAGCGCGCCAGGATCTTCCCCGTCCATACAAGTGTCCCCTGTGTGATCGCGCCTTCCATC   259
      luAlaArgGlnAspLeuProArgProTyrLysCysProLeuCysAspArgAlaPheHisA
  260 GTTTGGAGCACCAGACCAGACATATTCGCACACATACGGGTGAAAAGCCACACGCTTGCC   319
      rgLeuGluHisGlnThrArgHisIleArgThrHisThrGlyGluLysProHisAlaCysG
  320 AGTTCCCGGGCTGCACAAAACGCTTTAGTCGCTCTGACGAGCTGACACGCCACTCAAGAA   379
      lnPheProGlyCysThrLysArgPheSerArgSerAspGluLeuThrArgHisSerArgI
  380 TTCACAACAACCCCAACTCCAGGCGGAGTAACAAGGCACATCTGGCCGCTGCCGCTGCCG   439
      leHisAsnAsnProAsnSerArgArgSerAsnLysAlaHisLeuAlaAlaAlaAlaAlaA
  440 CTGCCGCTGCCGGACAAGAGAATGCAATGGTAAATGTGACCAACGCGGGCTCGTTGATGC   499
      laAlaAlaAlaGlyGlnGluAsnAlaMetValAsnValThrAsnAlaGlySerLeuMetP
  500 CCCCGCCCACAAAGCCTATGACCCGCTCTGCGCCTGTCTCTCAGGTTGGATCTCCGGATG   559
      roProProThrLysProMetThrArgSerAlaProValSerGlnValGlySerProAspV
  560 TCTCCCCTCCGCACTCCTTCTCGAACTATGCCGGTCACATGCGTTCCAATCTGGGACCAT   619
      alSerProProHisSerPheSerAsnTyrAlaGlyHisMetArgSerAsnLeuGlyProT
```

-continued

```
 620 ATGCTCGCAACACCGAGCGGGCGTCCTCGGGAATGGATATCAATCTACTTGCCACCGCTG    679
     yrAlaArgAsnThrGluArgAlaSerSerGlyMetAspIleAsnLeuLeuAlaThrAlaA

680 CATCTCAGGTTGAGCGTGATGAACAACATTTTGGGTTCCACGCTGGTCCACGTAATCACC    739
     laSerGlnValGluArgAspGluGlnHisPheGlyPheHisAlaGlyProArgAsnHisH

740 ATTTGTTCGCCTCGCGTCACCACACCGGTCGTGGCCTGCCTTCCCTTTCAGCGTACGCCA    799
     isLeuPheAlaSerArgHisHisThrGlyArgGlyLeuProSerLeuSerAlaTyrAlaI

800 TCTCGCACAGCATGAGCCGTTCTCACTTTCACGAGGACGAGGATGGTTACACTCATCGCG    859
     leSerHisSerMetSerArgSerHisPheHisGluAspGluAspGlyTyrThrHisArgV

860 TCAAGCGCTCAAGGCCTAACTCACCAAACTCGACCGCTCCGTCCTCACCGACTTTCTCTC    919
     alLysArgSerArgProAsnSerProAsnSerThrAlaProSerSerProThrPheSerH

920 ACGACTCTCTTTCCCCAACGCCAGACCACACTCCGTTGGCAACCCCTGCTCATTCGCCAC    979
     isAspSerLeuSerProThrProAspHisThrProLeuAlaThrProAlaHisSerProA

980 GCTTGAGGTCATTGGGATCTAGCGAACTCCACCTTCCTTCGATTCGCCATCTGTCCCTCC   1039
     rgLeuArgSerLeuGlySerSerGluLeuHisLeuProSerIleArgHisLeuSerLeuH

1040 ATCACACCCCTGCCCTTGCTCCAATGGAGCCCCAGCCGGAAGGCCCCAACTATTACAGTC   1099
     isHisThrProAlaLeuAlaProMetGluProGlnProGluGlyProAsnTyrTyrSerP

1100 CCAGCCAGTCTCATGGTCCCACAATCAGCGATATCATGTCCAGACCCGACGGAACACAGC   1159
     roSerGlnSerHisGlyProThrIleSerAspIleMetSerArgProAspGlyThrGlnA

1160 GTAAACTGCCCGTTCCACAGGTTCCCAAGGTCGCGGTGCAAGATATGCTGAACCCCAGCG   1219
     rgLysLeuProValProGlnValProLysValAlaValGlnAspMetLeuAsnProSerA

1220 CTGGGTTTTCGTCGGTTTCCTCATCGACGAATAACTCTGTCGCAGGAAATGATTTGGCAG   1279
     laGlyPheSerSerValSerSerSerThrAsnAsnSerValAlaGlyAsnAspLeuAlaG

1280 AACGTTTCTAGCCTGGTGCGGCTGCGAAACCCTTTCAATGTATAAAGTTTGGGCTCAAA    1339
     luArgPheEnd

1340 AAAAATTCTTGACTGTCATACGCGCTACGAAACGAATAGACTTTGTGCATTTACAGTGCG   1399
1400 TGGTTCATGGGCATCCTTGGTGTCGGCTGGCTTTCTTTGCTTACTTTGTTCGAGTATACT   1459
1460 TTTGCGAGGCGTCCATAGTGATAGACGGGTGGGATATTCTTGTGGCTTTTTCCGTGCTTG   1519
1520 TTCGATTCTCCCCTTTCGCTCTCCTTGAAAAATACCTTTCTTATCCTATAACCATTTGTT   1579
1580 TCATTATCCCAATGGGAATTGGCTCTACAGCTCTTATTCATTTTGTCTACTCCTCTCCTG   1639
1640 AGGCCCAGTCCCCTGATAATTCCGGGCTCTACCATATACATTTCATTTCGACTATGTCAG   1699
1700 TTTCCGCTTCGATTTAGACCTCGAGCAGGACGAGAGGGTTCCGAAAGAAAATACAAACAA   1759
1760 AAATTATAGTAATCTGCGTTTACTTTGGCATAATACAGTAGTCATTAGTTGAGGTAGGCA   1819
1820 TAATCTGGATGTCTAACCATCACTTGCCCTAACCTCCTACCATCTGCTGCTAGTATTTGT   1879
1880 CTTACCCGAAACCCAATTCAACGAGATAGATGGATTGACGAATAACAATTTGTTGTCCAG   1939
1940 CGACATGCATGATACATGCGTACGTACATACACTAATAGTAGTCACAGACCAGTTCATCA   1999
2000 CATCCTGGTCTCGGGTATTCAGATACGGAAATGCGTAAGATTGGAAGGGTCTAAGAAAAA   2059
2060 GCAAAGAAAAGGAAAAGTTAACACTGGCTGGCGCTCTCTTTCCATCTCTGATCAATGTT    2119
2120 ATTGTTCGTCACTCAGCTGTGGACGTGGCTCCAGTCAAGTTGTGAATTATGATAGGGTAT   2179
2180 TGTTGACTTGACAAGTTGATCTTGATGGAATCAAATCTTCTCCCCGCCAGATTCTGACGC   2239
2240 TTGAGGCTCTCGGATCGAATGAACAACTTTTCGCACCACATCAACCGGTTGCCGCGTGAT   2299
2300 GCTGGAGACAAACCGACCCAAACGTCACGGTCACACGGAGGATACGTTTGCTAGAGCCAG   2359
2360 CTGATACCCCAAGAGACAAGAAGGTAAAGGTCGCAAAAATCTTTTCAATAAGATGGCATC   2419
2420 TTCCCCCCACCAACCCTTAACCATTCTCCTTTCAAGCTGTGTTGCCCCGCTTTGGTGCAT   2479
2480 GGGCTTGGGTAGTGCGGTCGCAAAACTACTAATTTAATGACCGACTGCTGCTGCTTTTTC   2539
2540 ACTCGCCGCTCACGGACTAAGCATGTGGGAACAGGATCGCCCCGTCACTATTTCAGATCG   2599
2600 TGTCGTATCAAGGTGTTCGCCCGGTGCTGCTGGCACGAACGCCGGCCATCCAAGATCATT   2659
```

-continued

```
2660 GTTCTCATTCAAACCGGGCGGCTTACGTCTAGCCGCGGACGTAAGCACGAAGAGTGTGTG  2719

2720 TAGTGGTGGGAGTGAAGCCGTTGCCGAAACCATGCCGTCCTCCACGGCCGTCCCGTCGTT  2779

2780 ATCAAGCGACGCTGCCTCCGCTTCATCCTCATCAGCGGGTGTATCTCTGGAGACAAGATG  2839

2840 GGCGGAAGGTCTCACCGGCCAGGAGATATTAGAAGACGATGGAACGGGCGCGCTGCTCGT  2899

2900 CCCGCCGTCCCGCCCTGCTCGGCAATATCATCACCATACCTATATCTGTCTGTTCTATAT  2959

2960 CTTAGATTGTCACCACACCTTCGACGATGTCGAGCAATGGAAGACTCACGTTCTGAGCCA  3019

3020 CTTCCGAACCCACGAACCACCGCGAACAGCCCGATGCCCTCTATGTCCGGGTGAGCGGTT  3079

3080 CAGCGACACCCCCGAACAGAAAGGATGGGATCGCATGC                        3117
```

EXAMPLE 3

Genetic Modification of the creA Gene

In the DNA sequence stop codons were introduced at position +226-228 and +229-231, changing the sequence TACAAG encoding the dipeptide TyrLys into TAGTAG (StopStop). This mutation was introduced into pNFF212 by site directed mutagenesis using oligonucleotide CTTC-CCCGTCCATAGTAGTGTCCCCTGTG (SEQ ID NO 3) and its complement CACAGGGGACACTACTATG-GACGGGGAAG (SEQ ID NO 4) as described in the Quickchange protocol (Stratagene, Basel).

This mutation results in a truncation of the creA gene product N-terminal of the DNA binding zinc finger domain, rendering it inactive. By introducing this construct into the *A. oryzae* NF2 (CNCM 1882, EP 97111378.2), creA-areA double mutants could be selected directly on plating the microorganisms on MM plates containing 0.2% soy protein and 50 mM glucose solidified with 2% agar noble.

EXAMPLE 4

Modification of the creA Gene

Further, the creA gene was deleted from the molds genome as follows. pNFF212 was partially digested with EcoRI and the linear molecule was recovered from an agarose gel. After dephosphorylation and ligation to the 1843 bp *A. nidulans* pyrG fragment from pNFF38 (A. Doumas, P van den Broek, M. Affolter, M. Monod (1998) Characterisation of the Prolyl dipeptidyl peptidase gene (dppIV) from the Koji mold *Aspergillus oryzae*, Applied and Environmental Microbiology 64, 4809-4815), pNFF234 was generated. In pNFF234, the creA coding region is interrupted by a functional *A. nidulans* pyrg gene, truncating the gene product immediately downstream of the DNA binding zinc finger.

To obtain a creA mutant, pNFF234 was digested with BstXI and introduced into *A. oryzae* NF1 by transformation. The primary transformants are selected on MM without uridine and screened for hypersensitivity towards allyl-alcohol and Fluor-acetate in the presence of 50 mM glucose. Sensitive transformants were then tested for the desired gene replacement by Southern analysis or PCR.

EXAMPLE 5

Test for Expression

In order to further prove a mutation in the creA gene several tests were performed.

1) Amylase Test

The strains obtained in example 1 were grown on minimal medium (supra) containing 1% starch and 50 mM glucose as carbon source. Under these conditions wild type strains, in which the amylases are repressed by glucose, will not produce a halo when stained with a KI solution. In contrast thereto a creA mutant will produce a halo, since amylase expression is no longer repressed by glucose. All three colonies isolated in example 1 did produce a halo.

2) Acetamidase Test

Strains can also be assayed for acetamidase activity when grown on a minimal medium (supra) containing acetamide and glucose as carbon source. Under these conditions wild type strains do not produce acetamidase activity, whereas a creA mutants do.

3) Halo Production

On minimal medium plates containing 1-% skimmed milk and 50 mM glucose (initially turbid appearance of the plate) creA mutants exhibit a halo after 2 days at 30° C., whereas wild type strains do not.

The invention claimed is:

1. A method for enhancing the proteolytic activity of a koji mold belonging to the genus *Aspergillus, Rhizopus, Mucor*, or *Penicillium*, comprising modifying a creA gene of said koji mold such that the gene product thereof exhibits no binding affinity to DNA sequences that are responsible for blocking the transcription of a protease, thereby enhancing the production of the protease in the koji mold.

2. The method according to claim 1 wherein the creA gene is not transcribed to a mRNA capable to be translated to a functional polypeptide.

3. The method according to claim 1 wherein the creA gene has been deleted.

4. The method according to claim 1 wherein the koji mold is *Aspergillus oryzae* CNCM I-2165 (NF14).

5. The method according to claim 1 wherein an areA gene of the koji mold is overexpressed.

6. A method for preparing a protein hydrolysate from hydrolyzing a proteinaceous material with a koji mold belonging to the genus *Aspergillus, Rhizopus, Mucor*, or *Penicillium*, comprising modifying a creA gene of said koji mold such that the gene product thereof exhibits no binding affinity to DNA sequences that are responsible for blocking the transcription of a protease, thereby enhancing the production of the protease in the koji mold; and contacting said proteinaceous material with said koji mold.

* * * * *